(12) United States Patent
Poole

(10) Patent No.: US 8,211,698 B2
(45) Date of Patent: Jul. 3, 2012

(54) METHODS OF DERIVATION OF NEURONAL PROGENITOR CELLS FROM EMBRYONIC STEM CELLS

(75) Inventor: Aleksandra Jovanovic Poole, Irvine, CA (US)

(73) Assignee: California Stem Cells, Inc., Irvine, CA (US)

( * ) Notice: Subject to any disclaimer, the term of this patent is extended or adjusted under 35 U.S.C. 154(b) by 291 days.

(21) Appl. No.: 12/185,695

(22) Filed: Aug. 4, 2008

(65) Prior Publication Data
US 2009/0175834 A1   Jul. 9, 2009

Related U.S. Application Data

(60) Provisional application No. 60/963,281, filed on Aug. 2, 2007.

(51) Int. Cl.
*C12N 15/00* (2006.01)

(52) U.S. Cl. ........ 435/377; 435/378; 435/380; 435/383; 435/395

(58) Field of Classification Search ........................ None
See application file for complete search history.

(56) References Cited

U.S. PATENT DOCUMENTS

| 2003/0068819 A1 | 4/2003 | Zhang et al. | |
|---|---|---|---|
| 2006/0073587 A1* | 4/2006 | Stice et al. | .................... 435/325 |

FOREIGN PATENT DOCUMENTS

| EP | 1 302 536 A2 | 10/2002 |
|---|---|---|
| WO | 01/88104 A2 | 11/2001 |
| WO | 2004/099395 A2 | 11/2004 |
| WO | 2006/044204 A2 | 4/2006 |

OTHER PUBLICATIONS

<http://stemcells.nih.gov/info/glossary.asp>.*
Perrier et al. Derivation of midbrain dopamine neurons from human embryonic stem cells PNAS, 2004, vol. 101, pp. 12543-12548.*
Ben-Hur, T., et al., Transplantation of Human Embryonic Stem Cell-Derived Neural Progenitors Improves Behavioral Deficit in Parkinsonian Rats, Stem Cells, 2004, 22:1246-1255.
Carpenter, M.K., et al., Enrichment of Neurons and Neural Precursors from Human Embryonic Stem Cells, Experimental Neurology, 2001, 172:383-397.
Reubinoff, B.E., et al., Neural Progenitors from Human Embryonic Stem Cells, Nature Biotechnology, 2001, 19:1134-1140.

* cited by examiner

*Primary Examiner* — Deborah Crouch
(74) *Attorney, Agent, or Firm* — Baker & Hostetler LLP; Mark H. Krietzman

(57) ABSTRACT

The invention provides neuronal progenitor cells, populations and cultures of cells, cell compositions and methods of producing neuronal progenitor cells. Neuronal progenitor cells can be prepared from embryonic stem cells, such as human embryonic stem cells.

14 Claims, 5 Drawing Sheets

METHODS OF DERIVATION OF NEURONAL PROGENITOR CELLS FROM EMBRYONIC STEM CELLS

RELATED APPLICATIONS

This application claims benefit of priority of U.S. Application Ser. No. 60/963,281, filed Aug. 2, 2007, which is expressly incorporated herein by reference.

FIELD OF THE INVENTION

The invention relates to neuronal progenitor cells, compositions and methods to generate neuronal progenitor cells in which a large proportion of the cells in a cell culture or population of cells are neuronal progenitor cells. Neuronal progenitor cells can be prepared from embryonic stem cells. Additionally, the invention relates to methods of expanding (proliferating) and propagating neuronal progenitor cells and administering or delivering such neuronal progenitor cells by transplantation or implantation into the central nervous system of an animal, such as a mammal (e.g., human).

INTRODUCTION

Neurons are known as terminally differentiated cells, incapable of further replication. In vitro manipulation of mature neurons is difficult and inefficient. Sources of immature/dividing neuronal cells have been reported to be found and used, but as therapeutical perspective these methods fail to satisfy one or more conditions required of a human therapy. Normal neuronal progenitors were reported to be isolated from subventricular areas of the immature fetal or mature /adult brain, which could differentiate in neurons and glia. Neuronal cell lines were also reported to be isolated from diverse tumors (neuroblastoma, pheochromocytoma) but have less therapeutic potential since these lines carry neoplastic characteristics.

Embryonic stem cells can differentiate into any type found in the body. The invention provides, among other things, high purity cultures and populations of neuronal progenitor cells, compositions including neuronal progenitor cells and methods procedures for obtaining and using neuronal progenitor cells. Such neuronal progenitor cells can be produced using a renewable source of embryonic stem cells. Neuronal progenitor cell cultures and populations include cultures and populations with minimal non-neuronal contaminant cells, such as glia (e.g., astrocytes).

During development, non-differentiated cells of the blastocyst will follow one of the germ layer lineages: ectoderm, mesoderm or endoderm. Ectodermal cells will undergo successive differentiation stages taking on of the three major pathways of External Ectoderm, neural crest and neural tube. External Ectoderm includes skin, epithelium of the mouth and nasal cavity, salivary glands, and glands of mouth and nasal cavity, enamel, epithelium of pineal and pituitary glands, lens and cornea of the eye, apical ectodermal ridge inducing development of the limb buds of the embryo and sensory receptors in epidermis. Neural crest includes dorsal root ganglia, Schwann cells, melanocytes, autonomic nervous system ganglia, facial cartilage, spiral septum (developing heart) and ciliary body (eye). Neural Tube includes brain, spinal cord, retina, posterior pituitary and adrenal medulla.

In the development of the central nervous system, multiple stages can be identified, each with defined characteristics, some cells giving rise of the cephalic portions (brain, retina) and other cell population to the caudal part—the spinal cord.

The fine differentiation of cellular subtypes in each of the CNS constituents is governed by general and especially by local factors.

SUMMARY

Disclosed herein are neuronal progenitor cells, cell cultures and cell populations, compositions of neuronal progenitor cells, and methods of producing small or large quantities of high purity, neuronal progenitors from human embryonic stem cells, which are of non-tumor origin. Such neuronal progenitor cells, cultures and populations, which can be derived from embryonic stem cells (e.g., human), are capable of following the normal subsequent developmental stages (differentiation, maturation) of neuronal progenitors, and can fully differentiate into mature functional neurons. Neuronal progenitor cells and progeny cells derived from neuronal progenitor cells, cell cultures, cell populations and compositions are useful in administration, delivery and transplantation/implantation into a subject in need thereof, such as a subject in need of neuronal progenitor cells or cells derived or differentiated therefrom. Such cells have been successfully transplanted into a host animal where the cells integrate into the appropriate central nervous system tissue (e.g., spinal cord tissue). Neuronal progenitor cells and progeny cells derived from neuronal progenitor cells, cell cultures and cell populations and compositions, such as mature neurons, are also useful in drug screening and in administration and delivery to a subject in need thereof.

In accordance with the invention, there are provided neuronal progenitor cells, cultures, populations and compositions. In one embodiment, a culture or population or composition of neuronal progenitor cells has a purity at or greater than about 60%, 70% or 75% neuronal progenitor cells as a percentage of the total number of cells in the culture, population, or compositions. In additional embodiments, the number of cells not considered to be neuronal progenitor cells in a culture or population or composition is less than about 30%, 25%, 20%, 15%, 10%, 5% of the total number of cells within the population, culture or composition.

In accordance with the invention, there are methods of producing neuronal progenitor cells, cultures, populations and compositions. In one embodiment, a culture or population or composition of neuronal progenitor cells is produced by: culturing or growing totipotent stem cells (e.g., embryonic stem cells, such as human) in a growth medium for a period of about 1-7 days, wherein the growth medium comprises basic fibroblast growth factor (bFGF) or fibroblast growth factor 2 (FGF2), and wherein the growth medium is without animal serum and without bone morphogenic proteins BMP2, BMP4 and BMP7, thereby producing a cell population in which a proportion of the cells are committed to ectoderm differentiation; and culturing or growing the cell population or a portion thereof produced therefrom in suspension (non-adherent conditions) in a growth medium for an additional period of about 5 to 10 days, wherein the growth medium comprises basic fibroblast growth factor (bFGF) or fibroblast growth factor 2 (FGF2), wherein the growth medium is without animal serum and without bone morphogenic proteins BMP2, BMP4 and BMP7, changing the growth media one or more times every 12 to 72 hours or providing media by a continuous flow system, thereby producing a cell population in which a proportion of the cells are neuronal progenitor cells.

Neuronal progenitor cells can be expanded (proliferated) and propagated. Thus, in accordance with the invention, there are provided neuronal progenitor cells, cultures, populations and compositions, in which the neuronal progenitor cells have been proliferated or expanded to produce additional daughter neuronal progenitor cells. In one embodiment, neuronal progenitors have been cultured or grown under conditions where the purity of the population, culture or composition has expanded (proliferates) and has attained or is maintained at greater than 60%, 70%, 75%, purity or more after one or more cell doublings (e.g., 1, 2, 3, 4, 5, 6, 7, 8, 9, 10 or more doublings). Such expanded or proliferated cells, cultures, populations and compositions can include 100,000, 5000,000, 1,000,000, 2,000,000-5,000,000 or more neuronal progenitor cells.

Neuronal progenitors stably or transiently express one or more neuronal marker. limiting Examples of developmental markers that can be expressed (detected) include HNF-3β (hepatocyte nuclear factor-3β), Pax3, Pax6, Shh (Sonic Hedgehog), Lhx3 (LIM homeobox protein 3), Chx10 (ceh-10 homeodomain containing homolog), Pax7, H4C4 (hyaluronate receptor, CD44), VIN-IS-53, AC4, FP3, NOT1, Wnt1 (wingless-type MMTV integration site family, member 1), ChAT (choline acetyltransferase), Isl1 (Islet 1), nestin. Examples of neuron markers include MAP2 (microtubule associate protein), NF200 (neuro-filament 200), Tuj 1 (neuron specific β III tubulin) and NeuN (Neuronal nuclei).

Neuronal progenitors can differentiate into various neuronal cell types. Thus, in accordance with the invention, there are provided neuronal progenitor cells, cultures, populations and compositions, in which the neuronal progenitor cells have been differentiated into or towards mature neurons, thereby forming a more differentiated or mature population of progenitor cells, such as a cell that is a developmental intermediate with respect to the neuronal progenitor cells and mature neurons, or mature neurons. In one embodiment, neuronal progenitors have been cultured or grown under conditions where the neuronal progenitor cells have differentiated into a developmental intermediate with respect to the neuronal progenitor cells and a mature neuron. In another embodiment, neuronal progenitors have been cultured or grown under conditions where the neuronal progenitor cells have differentiated into mature neurons. In such embodiments, developmental intermediate cells with respect to the neuronal progenitor cells, mature neurons, and cultures, populations and compositions that include developmental intermediate cells with respect to the neuronal progenitor cells or mature neurons are thereby provided.

The invention further provides methods of delivery and administration of neuronal progenitor cells, cultures, populations and compositions. In one embodiment, neuronal progenitors are delivered or administered (transplanted) to a subject in need thereof. Such subjects can therefore be treated by these methods. In such subjects, neuronal progenitor cells, cultures, populations or compositions include cells that remain viable after in vivo delivery or administration. In particular aspects, viability of the delivered, administered (transplanted) cells is greater than about 70%, 80%, 90%, 95% or 98%. Viable cells include neuronal progenitor cells, developmental intermediate cells with respect to the neuronal progenitor cells or mature neurons derived from neuronal progenitor cells, or a combination of progenitor, intermediate and mature neuron cells.

The invention moreover provides methods of delivery of neuronal progenitor cells, cultures, populations and compositions where the neuronal progenitor cells have differentiated into a developmental intermediate cell with respect to the neuronal progenitor cells, or a mature neuron. In one embodiment, cells that are developmental intermediates with respect to the neuronal progenitor cells and mature neurons, or mature neurons, cultures, populations or compositions of such cells are delivered or administered (transplanted) to a subject in need thereof. In such subjects, the developmental intermediate cells (or mature neurons derived therefrom) remain viable after in vivo delivery or administration (e.g., viability of the delivered, administered (transplanted) cells is greater than about 70%, 80%, 90%, 95% or 98%).

Methods of delivery further include shipping or transporting the cells, cultures, populations or compositions from one location to another, e.g., an origin location to destination location. Such methods in particular embodiments include shipping or transporting from the origin location under conditions in which all or a subset of the cells retain viability (e.g., viability is at or greater than about 40%, 50%, 60%, 70%, 75%, 80%, 85%, 90%, 95% or more, such as 96%, 97%, or 98%), optionally over long distances (e.g., 500, 1,000, 5,000 or more miles) with cells arriving ready for use at the destination location. In particular aspects, cell viability is maintained by temperature control, for example, packaging that can maintain a temperature within a certain range (e.g., 20-30 deg C.).

Neuronal progenitor cells, cells that are developmental intermediates with respect to the neuronal progenitor cells and mature neurons, and mature neurons can be used to screen or evaluate a compound or agent (e.g., drug candidate) for treatment of a neural disease or disorder. Thus, in accordance with the invention, there are provided methods of screening, identifying and evaluating a compound or agent using neuronal progenitor cells, cells that are developmental intermediates with respect to the neuronal progenitor cells and mature neurons, and mature neurons, populations, cultures and compositions thereof. In one embodiment, cells (e.g., neuronal progenitor cells, developmental intermediate cells or mature neurons) are contacted with a compound or agent (e.g., drug candidate), and determining if the compound or agent (e.g., drug candidate) modulates an activity or function of the cells.

Neuronal progenitor cells, cells that are developmental intermediates with respect to the neuronal progenitor cells and mature neurons, and mature neurons can be included in a kit. Thus, in accordance with the invention, there are provided kits that include neuronal progenitor cells, cells that are developmental intermediates with respect to the neuronal progenitor cells and mature neurons, and mature neurons, cultures, populations and compositions. In one embodiment, a kit includes cells disposed in a dish or plate, such as a multi-well plate (e., 4, 6, 8, 12, 4, 36, 48, 96, 384, 1536 well plates), wherein one or more of the wells of the plates include the cells. Such kits can include materials to maintain sterility, viability and minimize leakage or loss of any liquids or gasses present in the kit, or in contact with the plate, well, or cells therein.

DETAILED DESCRIPTION

Figure 1:
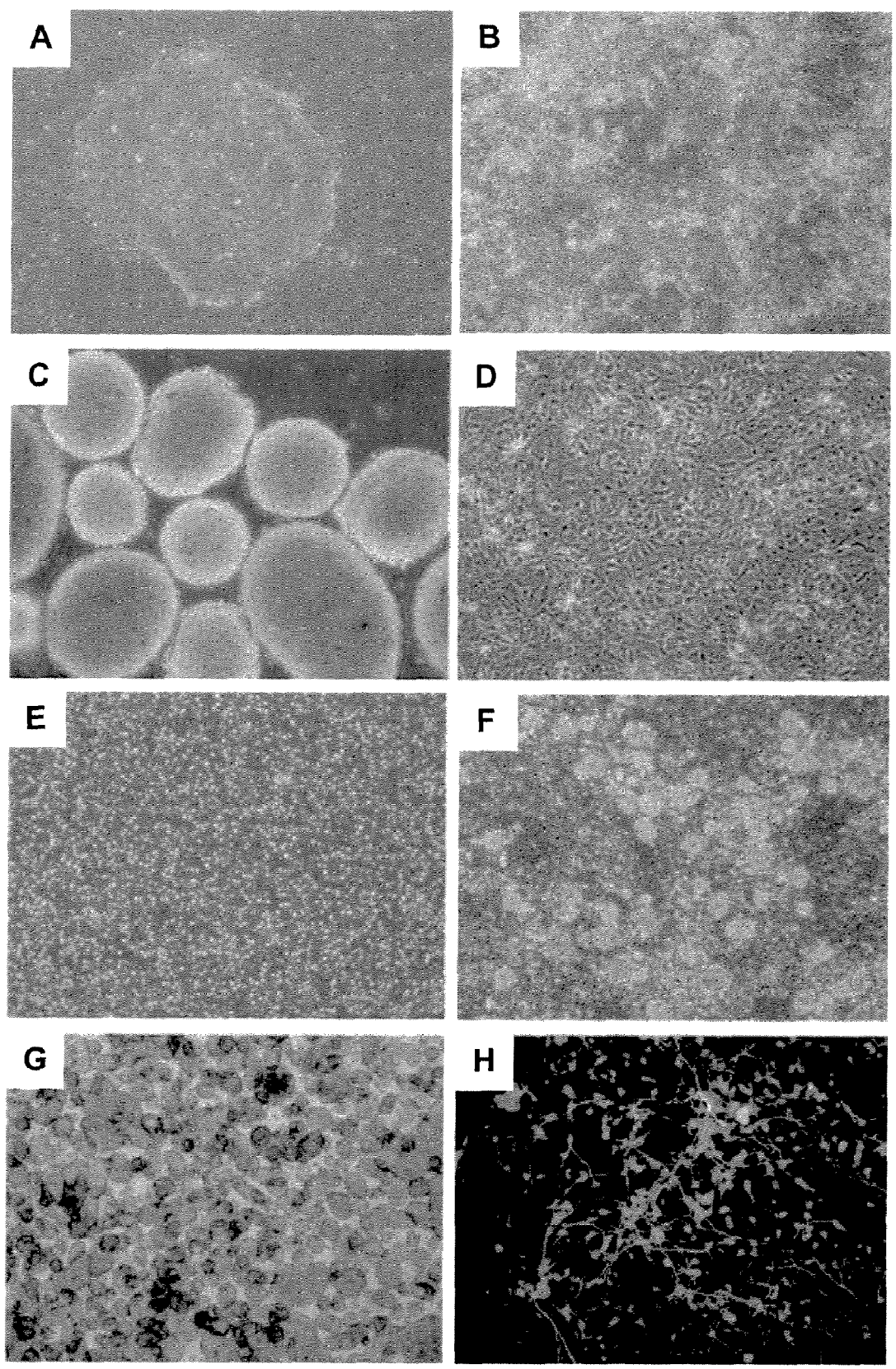
FIGS. 1A-1D show human embryonic stem cells grown on Matrigel: A) Induction stage with visible neuronal tendencies (small triangular cells forming rosettes); B) dissociated cultures in non adherent system. Floating clumps of different size containing neuronal progenitor cells; C) plated neuronal progenitors in high density; D) dissociated culture using Trypsin; E) Aggregation of the single cell suspension after 24 hours; F) Separation of the clustered cells from the single floating cells; G) Concentration to the desired ~100,000 cells/µl; and H) Tuj1 positive neurons with very few GFAP positive cells after 3 more passages.
Figure 2:
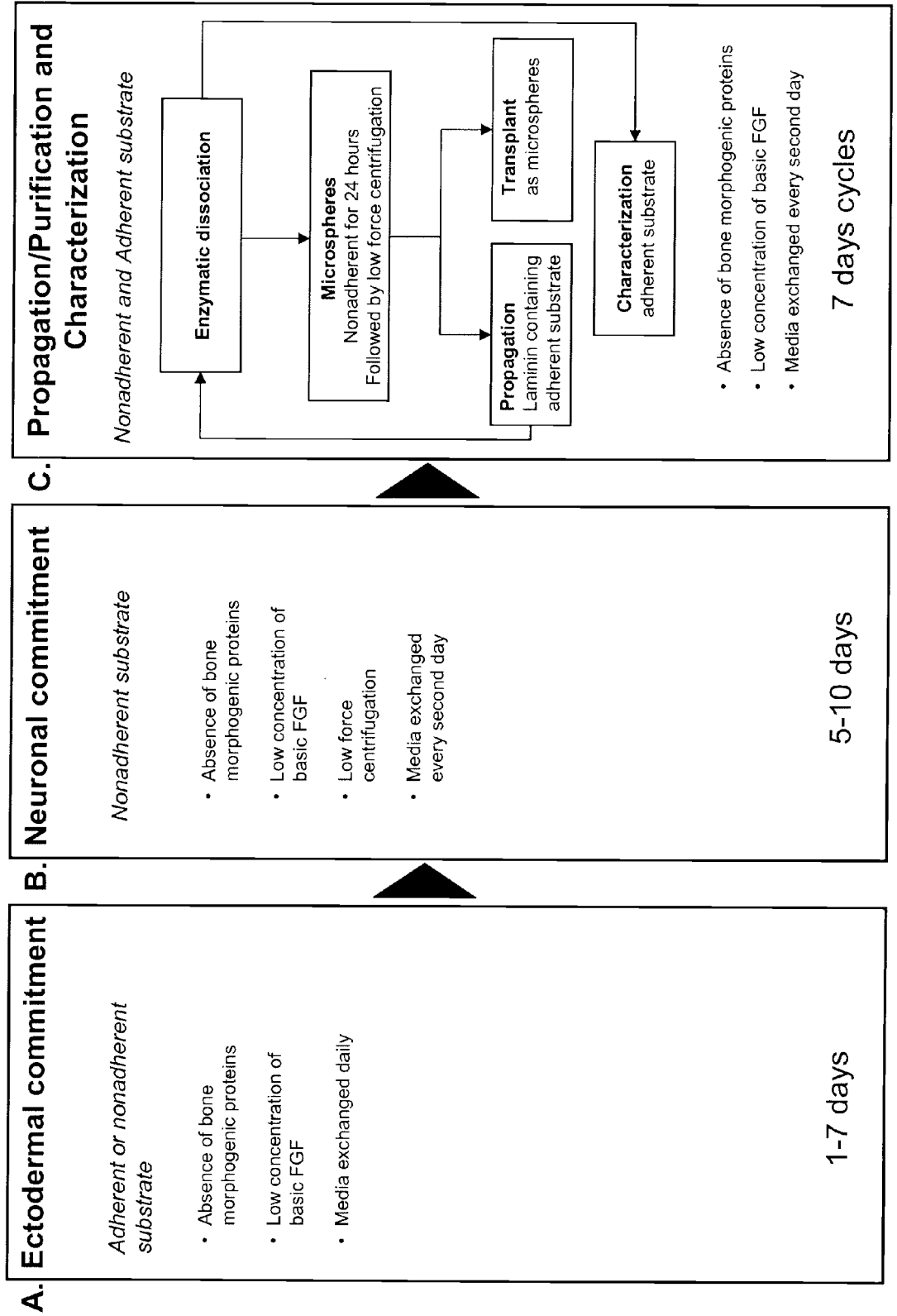
FIGS. 2A-2C illustrate an exemplary overall general scheme of a method of the invention: A) Ectodermal commitment; B) Neuronal commitment; C) Propagation, Purification and Characterization
Figure 3:
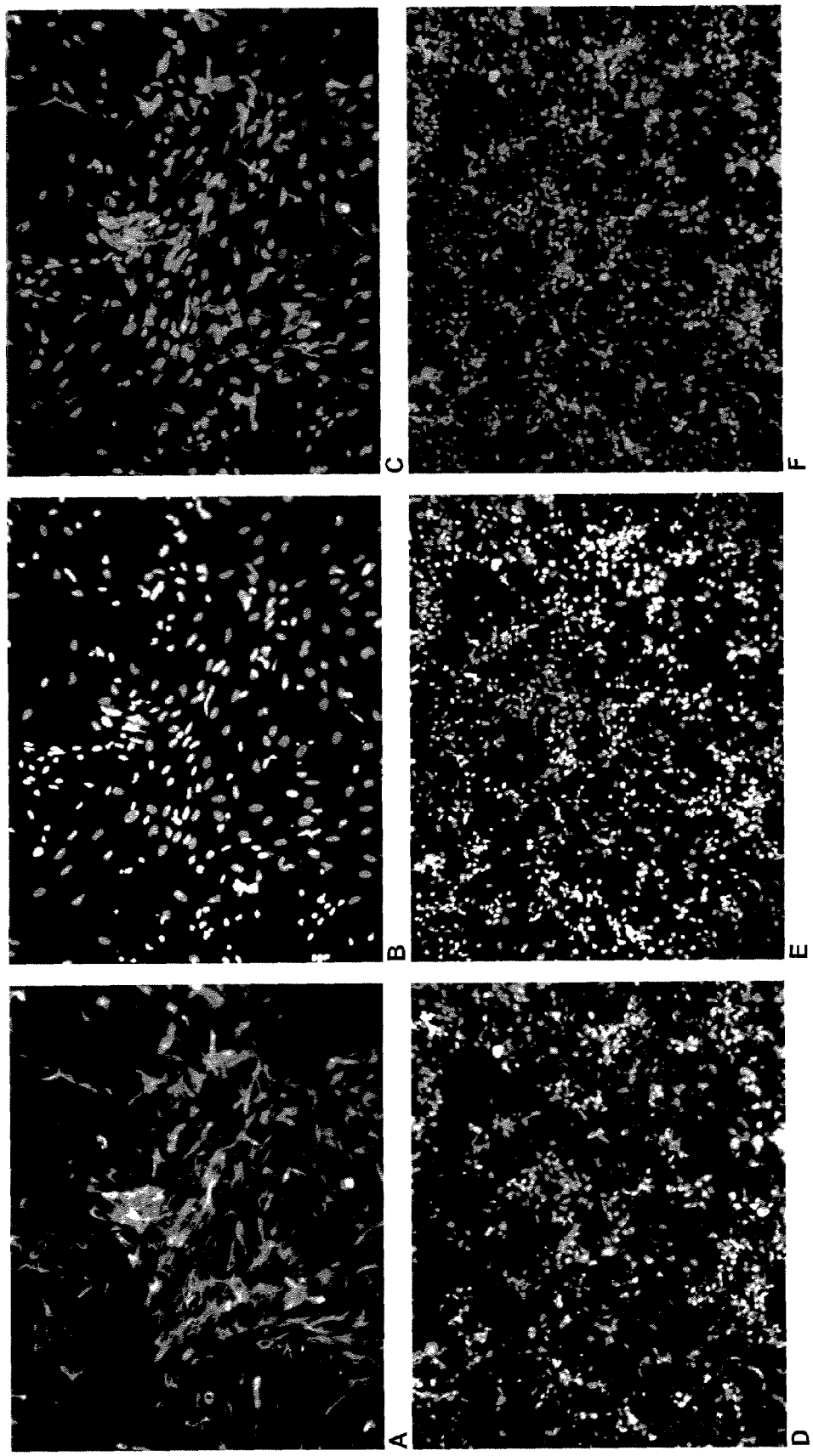
FIGS. 3A-3F show neuronal progenitors in vitro derived from human embryonic stem cell (Magnification 40X) A) stained with Anti nestin; B) bisbenzimide nuclear counterstain; and C) merged images 3A and 3B; and (Magnification 20×) D) neuronal progenitors labeled for the transcription factor Pax 6; E) nuclear counterstain; and F) merged images of 3D and 3F.
Figure 4:
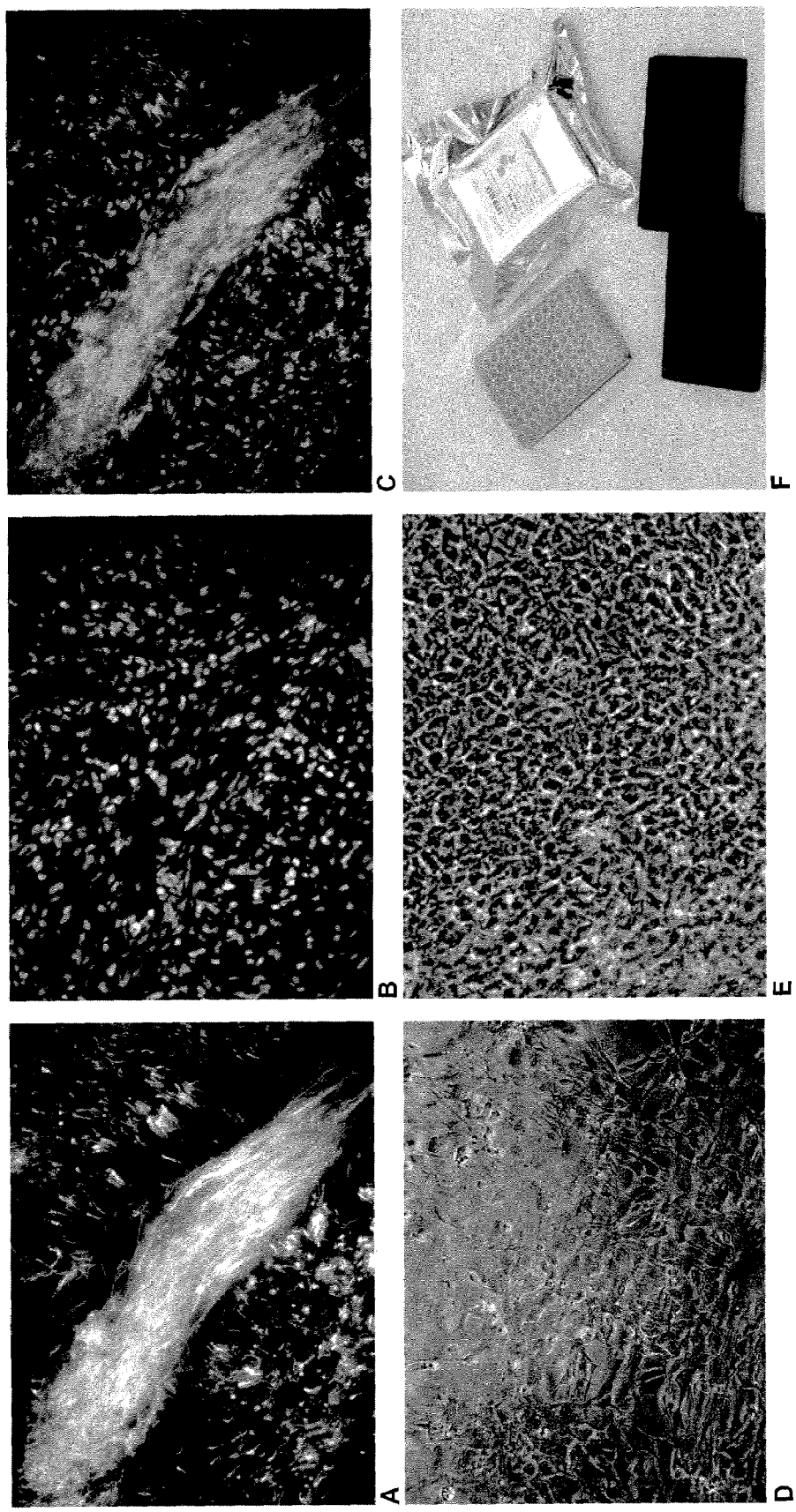
FIGS. 4A-4F show human neuronal progenitors transplanted into rat spinal cord at 40× Magnification, A) anti-human Tuj1, specific for neuronal branching (red on merged image); B) anti-human nuclear labeling of the transplanted cells (green on merged image); and C) merged images of 4A and 4B; and neuronal progenitors plated in 96 well test plates at 20× Magnification, D) neuronal progenitors; E) phase contrast image; and F) packaging of the multi-well plates. The vacuum sealed plastic bag is placed inside of a Mylar pouch and thermo-sealed.
Figure 5:
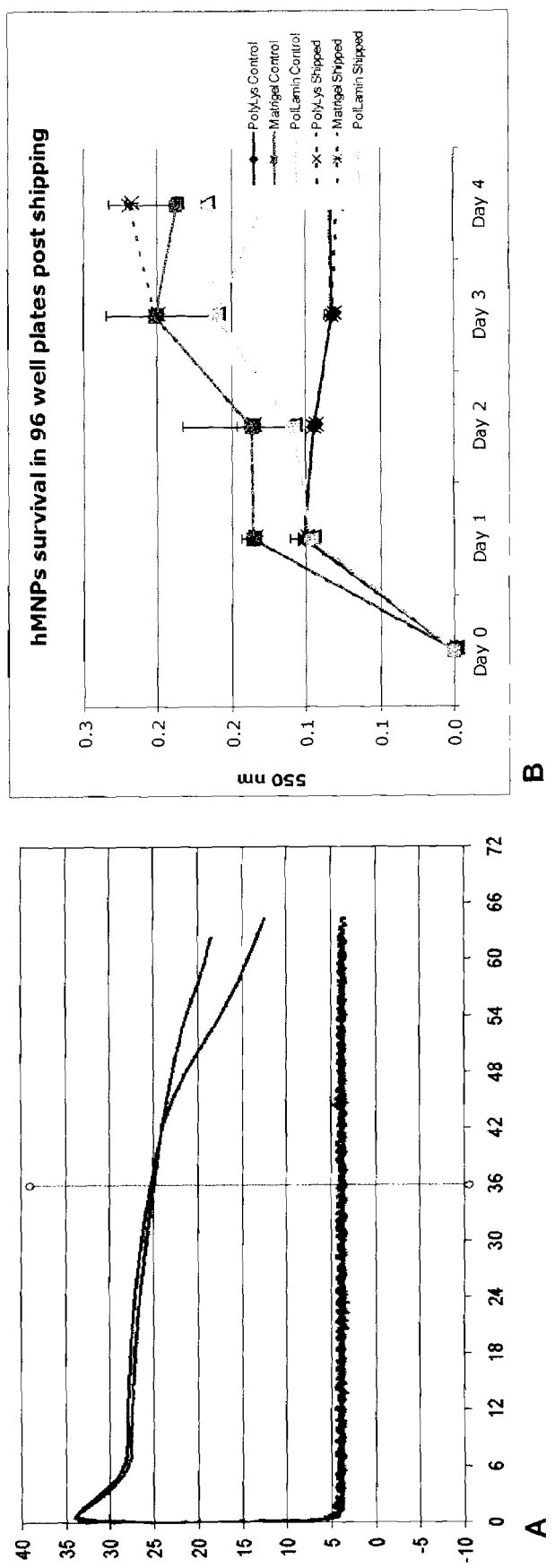
FIGS. 5A-5B illustrate A) temperature characteristics inside of the package, during transportation—temperature is maintained for 36 hours within 25'-30° C. and within 20° and 30° C. for up to 48 hours; and B) survival at destination after shipping, as analyzed using an automated plate reader (Molecular Devices). The curves represent various substrates to test the optimal plating conditions.

The invention provides cells, cultures, populations and compositions in which there are greater than about 50%, 60%, 70%, 75%, 80%, 85%, 90%, 95% of neuronal progenitors of the total number of cells, optionally characterized by expression of a neuronal progenitor cell marker and the ability to differentiate into mature neurons. In particular embodiments, an isolated population of neuronal progenitor cells (e.g., human) has a purity greater than about 60%, 70%, or 75%; a purity of between 75% and 95%; a purity of between 90% and 100%. In additional particular embodiments, an isolated population of neuronal progenitor cells (e.g., human) has no more than about 30%, 25%, 20%, 15%, 10% or 5% non-neuronal cells in the isolated population. In particular aspects, there are no more than about 30%, 25%, 20%, 15%, 10% or 5% astrocytes, oligodendrocytes or fibroblasts in the isolated population.

Invention cells, cultures, populations and compositions can have a reduced purity or amount of neuronal progenitors (e.g., 50, 60, 70% neuronal progenitors), and at the end of one or more method steps have an increased relative proportion of neuronal progenitor cells within the population, culture or composition, e.g., 70%, 75%, 80%, 85%, 90%, 95% or more are neuronal progenitors. In the cells, cultures, populations and compositions, typically less than about 30%, 25%, 20% or about 15%, or about 10%, or about 5%, or less of the cells are non-neuronal cells.

Neuronal progenitor cells can be characterized by transient or stable expression of a neuronal marker. Neuronal progenitor cell developmental markers include HNF-3b (hepatocyte nuclear factor-3beta), Pax3, Pax6, Shh (Sonic Hedgehog), Lhx3 (LIM homeobox protein 3), Chx10 (ceh-10 homeodomain containing homolog), Pax7, H4C4 (hyaluronate receptor, CD44), VIN-IS-53, AC4, FP3, NOT1, Wnt1 (wingless-type MMTV integration site family, member 1), ChAT (choline acetyltransferase), Isl1 (Islet 1), nestin. Neuron markers include MAP2 (microtubule associate protein), NF200 (neuro-filament 200), Tuj 1 (neuron specific β III tubulin) and NeuN (Neuronal nuclei). Thus, by such criteria, non-neuronal progenitor cells are those that do not express one or more specific markers, as determined by a detection assay, for example, immunocytochemistry, flow cytometry or fluorescence activated cell sorting (FACS).

Neuronal progenitors can also be characterized by morphology. In particular non-limiting embodiments, a neuronal progenitor is characterized as forming cell aggregates or agglomerates in suspension (non-adherent conditions), or forming a multi-cell layer in an adherent substrate. Typically, one or more of the cell aggregates or multi-cell layer include about 10-500 neuronal progenitor cells. In additional non-limiting embodiments, a neuronal progenitor is characterized as exhibiting one or more of the following characteristics: a small oval or triangular cell shape with minimal cytoplasm; unipolar or bipolar with short expansions/processes optionally with a spliced termination; active cell division on the longitudinal axis; or a polarized orientation; limited migratory ability. In further non-limiting embodiments, adding a basic or acidic fibroblast growth factor (FGF1 or FGF2) at a concentration of about 4-20 ng/ml, or adding insulin-like growth factor (IGF) at a concentration of about 10-100 ng/ml to the cells, or contacting the cells with fibroblasts or myoblasts or a product of fibroblasts or myoblasts causes one or more of the neuronal progenitor cells to retract one or more of expansions/processes, reassemble into a flat, epithelial morphology, or acquire an ability to migrate or replicate. Thus, by such criteria non-neuronal cells may not have one or more the forgoing morphological characteristics.

Neuronal progenitor cells can further be characterized by an ability to terminally differentiate into mature neurons. Thus, non-neuronal cells do not typically terminally differentiate into mature neurons.

Non-limiting examples of non-neuronal cells that may be in the population, culture or composition of neuronal progenitor cells include but are not limited to glial cells (astrocytes, oligodendrocytes) and fibroblasts. Astrocytes are a typical contaminant cell and can represent up to about 35% of the cells, but are typically less than 35%, e.g., about 30%, 25%, 20%, 1%, 10%, 5% or less. Other contaminant cells that may be present include oligodendrocytes and fibroblasts. Such cells may represent less than 30%, 25%, 20%, 15%, 10%, 5% or less, e.g., 1%.

In embodiments of the invention in which neuronal progenitor cells are identified by transient or stable expression of a marker, morphology or the ability to terminally differentiate into a neuron, not all cells within a plurality of cells, a population of cells, a culture of cells or a composition need to express a particular marker, have a particular morphology or be capable of differentiating into a neuron. Thus, in any given plurality, population, culture or compositions of neuronal progenitor cells some individual cells will not express a particular marker, have a particular morphology or be capable of differentiating into a neuron. The features indicative of neuronal progenitor cells, such as expression of a marker, cell morphology and ability to terminally differentiate into neurons is viewed in terms of the plurality of cells, and not in terms of any one individual cell.

As used herein, a "cell population" refers to a plurality or a collection of cells. A cell population can have greater or less numbers of particular cells than other cells present in the population.

A "cell culture" refers to maintenance or growth of one or more cells in vitro or ex vivo. Thus, a cell culture is one or more cells in a growth or culture medium of some kind. A "culture medium" or "growth medium" are used interchangeably herein to mean any substance or preparation used for sustaining or maintaining viability of cells, or growing cells.

Cell cultures can take on a variety of formats. For example, an "adherent culture" refers to a culture in which cells in contact with a suitable growth medium are present, and can be viable or proliferate while adhered to a substrate. A "non-adherent culture" refers to a culture in which cells are typically in suspension with a suitable growth medium, and can be viable or proliferate while not being adhered to a substrate. Likewise, a "continuous flow culture" refers to the cultivation of cells in a continuous flow of fresh medium to maintain cell viability, e.g. growth.

Neuronal progenitor cells include individual cells, and populations and pluralities of cells (or progeny) that are isolated or purified. As used herein, the terms "isolated" or "purified," and grammatical variations thereof, refers to made or altered "by the hand of man" from the natural state i.e. when it has been removed or separated from one or more components of the original natural in vivo environment. An isolated cell can but need not be substantially separated from other biological components of the organism in which the composition naturally occurs. An example of an isolated cell would be a neuronal progenitor cell obtained from a totipotent cell, such as an embryonic stem cell (e.g., human or hESC). "Isolated" also refers to a cell, for example, a cell separated from one or more contaminants (i.e. materials an substances that differ from the cell).

The term "purified" refers to a composition free of many, most or all of the materials with which it typically associates with in nature. Thus, a neuronal progenitor cells is considered to be substantially purified when separated from other cells. Purified does not require absolute purity. Furthermore, "purified" cells can be combined with one or more other molecules. Thus, the term "purified" does not exclude combinations. Purified can be at least about 40%, 50%, 60%, 65%, 70%, or more by numbers or by mass. Purity can also be about 75% or 80% or more, and can be greater, for example, 85% or 90% or more. Purity can be less, for example, in a pharmaceutical carrier the amount of neuronal progenitor cells or progeny thereof or molecule by weight percent (%) can be less than 50% or 60% of the mass by weight, but the relative proportion of the cells or molecule compared to other components with which it is normally associated with in nature will be greater. Purity of a population or composition of cells can be assessed by appropriate methods that would be known to the skilled artisan.

The invention further provides progeny of neuronal progenitor cells. A progeny cell refers to any and all cells descended or derived from neuronal progenitor cells by way of cell division, which include all descendents of the first, second, third and any and all subsequent generations and cells taken or obtained from such cells. Progeny cells therefore include clonal proliferation (e.g., daughter neuronal progenitor cells) and cells that are more mature or differentiated relative to neuronal progenitor cells due to differentiation or maturation. Specific non-limiting examples of cells that are more differentiated or developmentally mature relative to neuronal progenitor cells include cells that are a developmental intermediate cell between neuronal progenitor cells and fully differentiated neurons, as well as mature neurons. A "developmental intermediate" cell refers to any cell that is either a progeny cell that is distinct from fully differentiated neurons.

The term "derived" or "originates," when used in reference to a cell means that the cell or a parental cell of any previous generation at one point in time originated from a neuronal progenitor cell or progeny thereof. Accordingly, neuronal progenitor cells are not limited to those from a primary cell culture or cell population, but can be any subsequent progeny thereof or any subsequent doubling of the progeny thereof provided that the cell has the desired morphology, phenotypic markers, maturation or differentiation capability, or any other characteristic feature set forth herein or that would be know to the skilled artisan for neuronal progenitor cells and progeny thereof.

The following is a general description of an exemplary method which also includes a description of the stages of differentiation, namely ectodermal commitment, followed by neuronal commitment, and then the optional cell propagation (cell expansion/proliferation) and/or cell purification.

Ectodermal Commitment

To initiate ectodermal commitment embryonic stem cells (e.g., human) are contacted with a chemically defined media, specifically not containing animal serum, as described herein. Ectodermal commitment can be initiated in adherent conditions, when the cells are attached to a substrate, or non-adherent conditions, when the stem cell colonies are dissociated in floating cellular agglomerates. After 1 to 7 days of differentiation on adherent substrate or under non adherent conditions, the culture, if under adherent conditions is dissociated and transferred to a non adherent culture system.

An adherent substrate can comprise a commercially available product (e.g. Matrigel™, which includes laminin, collagen IV and entactin), laminin, fibronectin, a combination of gelatin and laminin and or fibronectin, on which the stem cells were cultivated for the last passage. A non adherent culture system refers to a sterile culture vessel made of material or coated with a antibiofouling material (e.g. agar gel) in which cells are maintained in a suspension.

A media composition includes a nutriment solution of amino acids, carbohydrates, minerals and complex molecules like vitamins, antioxidants, hormones and cytokines. The media composition can be based on a commercially available formulation, for example but not limited to DMEM or DMEM:F12 mixture, a chemically defined media without serum components and in absence of the bone morphogenic proteins (BMP2 and BMP4), maintained in the absence of sternness sustaining factors (e.g. high concentration of FGF2, incubation with feeder cell populations). An amount of FGF2, for example, 4 to 10 ng/ml can be added to the feeding media. Noggin, an antagonist of BMP2 and BMP4, at a concentration of 5-20 ng/ml, can be used to increase the amount of the neuronal progenitor cells.

Neuronal Commitment

After the 1-7 day initial time period, if cells are cultured for another 5-10 days in non adherent conditions, the conditions used for ectodermal commitment will drive the ectodermal progenitors towards a neuronal fate. The resulting neuroectoderm can generate all cells of the nervous system: neurons and glia.

The following are exemplary conditions to drive the ectodermal cells to a high yield of neuronal progenitors: media changed daily or more frequently (e.g., 12-24 hrs), or a continuous flow media exchange system used to feed the cells during the first 3 to 10 days of differentiation; maintain or attain a proportion of stem cells to be at least 25% or more (e.g., more than 30%, 40% or 50%) relative to the proportion of other culture components (cells surrounding the stem cell colonies); include basic fibroblastic growth factor (bFGF or FGF2) in the media at a concentration of 4 to 10 ng/ml; and include retinoic acid at a concentration of 5-20 µM with the above factor(s) for 1-10 days.

If grown on an adherent substrate in the described serum free medium, after 1-7 days the cultures can be enzymatic dissociated and transferred to a non-adherent system for another 5-10 days. Too early a transfer to non-adherent conditions may remove the non-differentiated cells with good potential to become neuronal progenitors, while a late transfer may sustain the growth of cell contaminant, which can change the fate of the cultures resulting in a low yield of neuronal progenitor cells.

From non-adherent conditions, the cultures are transferred to an adherent substrate, starting with day 10 to 21 of differentiation. Too early of cell transfer to adherent conditions will cause expansion of contaminant cells (e.g., fibroblasts, myoblasts) and too late transfer will cause early terminal maturation of the neuronal progenitors and a limited ability of the cell clumps to undergo dissociation. Dissociation of the cell clumps is a spontaneous process after transfer to an adherent substrate—the cells migrate out from the aggregates. If cells in the clumps are mature, migration is limited and only neuronal branches are extended from the clumps. The ability to use the cells, for example, for in vivo or in vitro applications, is impaired if the cell clumps do not dissociate.

The feeding procedure in nonadherent stages (by sedimentation, low force centrifugation) or the media flow in a continuous feeding system, in adherent or in nonadherent stages, will remove non aggregating cells which are nonviable or contaminant types (e.g. fibroblasts).

The foregoing exemplary procedures will select for cellular aggregates which include neuronal progenitors. When plated on adherent substrate, cells will migrate from the cell agglomerates and continue differentiation.

Expansion and Propagation

After plating cellular aggregates on adherent substrate neuronal progenitors can be identified by a number of criteria, including morphology and marker expression. A typical morphology is a bipolar or triangular morphology. To expand or increase numbers of neuronal progenitor cells, while inhibiting, reducing or preventing de-differentiation or progression towards terminal differentiation of neuronal progenitors, certain conditions are used: changing growth medium with 24 to 48 hour complete renewal and provide adequate media volume to the cells (minimum 1 ml media per 10^6 cells) to avoid excess accumulation of local secretion products; maintain low (less than 25%) contaminant cells in the culture or population, including astrocytes, fibroblasts and myoblasts; use a defined amount of growth factor (e.g., FGF at 4-10 ng/ml); and use growth media free of serum components. Under such conditions the neuronal progenitors will continue to proliferate and expand and will occupy the entire culture surface in multilayered arrangements.

Conditions such as abundant non neuronal contaminant cells, specially mesodermal (mesenchimal) lineage cells for example myoblasts and fibroblasts; high concentration of the growth factor (over 10-20 ng/ml) or unusually high activity of some batches of the growth factor; and low quality components (for example, B27 supplement) each can inhibit proper differentiation of the neuronal progenitors and promote instead differentiation into other cell types (mesodermal) for example, or can cause back (de-) differentiation.

When the flask cannot accommodate the feeding volume for the amount of growing cells, the culture can be enzymatically dissociated and re-distributed into larger or multiple culture vessels. When treated with a proteolytic enzyme (e.g. Trypsin at various concentrations, such as 0.025% to 0.25%), the cells will retract expansions and detach from the substrate. After removal or dilution of the enzyme and resuspension in a nutriment media, the cells are left overnight in a low adherent condition (e.g. Corning ultra low binding culture vessels). In this condition the neuronal progenitors will reassemble spherical conglomerates of up to about 100-200 cells. Isolated, nonagregated cells are considered nonviable, or lacking the proprieties of neuronal progenitors (contaminants) and separated by sedimentation or low force centrifugation. This step because reduces or prevents the propagation of unwanted cells, dilutes or removes apoptotic signals with the cellular debris and enhances the purity of the neuronal progenitor cultures.

After purification, cell clusters are transferred on an soft adherent substrate which incorporate laminin, or fibronectin (e.g. Matrigel™, mixture of collagen/laminin, gelatin/laminin) or substrates without laminin (poly-lysine, poly-ornitine).

Characterization

As disclosed herein progenitor cells can be morphologically characterized by a variety of features including, but not limited to, a small oval or triangular body with minimal cytoplasm, unipolar or bipolar with short expansions and sometimes spliced terminations. Active division on the longitudinal axis combined with oval/triangular cellular bodies the clusters of neuronal progenitors will reassemble rosettes. The cells have a polarized orientation in close contact to each other and a limited migratory ability. The cells typically form multi-layered, high density cultures when allowed to grow to appropriate densities.

In certain conditions, when large quantities of growth factors are added or the culture is exposed to secretion products of other cell types (e.g. fibroblasts, myoblasts) the neuronal progenitors can retract the processes and re-assemble to a flat, epithelial morphology, with ability to migrate and replicate. In this stage the neuronal progenitors can de-differentiate or back-differentiate towards pluripotency, which can in turn generate again glial descendents, such as astrocytes or oligodendrocytes, or epithelial cells.

Developmental markers of the neuronal tube are abundant, and transiently expressed: HNF3β, Pax3, PAx6, Shh, Lhx3, Chx10, Pax7, H4C4(CD44), VIN-IS-53, AC4, FP3, NOT1, Wnt1, ChAT, Isl1, nestin. In this regard, a cell culture or population may include cells of multiple stages. Each developmental marker has a peak, and most of these developmental markers are expressed very early (e.g., Pax6 is expressed in about 20-30% of cells in the first week, increases to 50-60% in the second week and reaches 90-100% after week 3. Pax6 decreases after maturation/differentiation to complete disappearance in mature neurons), with minimal significance for the claimed population. Cells considered to be neuronal progenitors express Pax6, and a neuron specific marker, for example neurofilaments (e.g., .beta.-tubulin, Map2, NF200, Tuj 1) or NeuN. These markers are stably expressed in neuronal progenitors and during expansion (neuronal progenitor stage). After maturation (mature neurons) expression of these markers is typically lost.

More particularly, Pax6 is expressed in about 20-30% of cells in the first week, increases to about 50-60% of cells in the second week and reaches 90-100% cells after week 3 and during expansion. The neurofilaments (b-tubulin, Map2, NF200, Tuj1) are expressed from second week—20-30% and reach 50-75% in the second week. At the end of differentiation about 90-100% of the cell population. Neu-N is expressed starting at about week 2 in 10-20% of cells and reaches 90-100% when in mature stages or fully differentiated into neurons. At the end of the protocol and during expansion (week 3-4 or more), about 40-75% of cells being positive for Neu-N. Neuronal progenitor cells typically have at least one of the described morphological characteristics, will spontaneously aggregate in clusters in non adherent conditions and will be positive to a developmental marker. For example, Pax6 combined with a neurofilament (MAP2, NF200, Tuj1) and/or a neuronal nuclei marker (NeuN). The percentage can vary between 1% and 100% for a brief period of time, for example, expression for 1-2 days up to 10-14 days.

In accordance with the invention, there are provided methods of producing neuronal progenitor cells, populations, cultures and compositions thereof, as well as progeny cells of neuronal progenitor cells, which are expanded or proliferated neuronal progenitor cells, or a differentiated or mature progeny of neuronal progenitor cells, such as a developmental intermediate cell between neuronal progenitor cells and neurons and glial cells.

In one embodiment, a method includes culturing or growing totipotent cells (e.g., embryonic stem cells, such as human or hESC) in a growth medium for a period of about 1-7 days (in an adherent substrate or in non-adherent condition or suspension), wherein the growth medium comprises, basic fibroblast growth factor (bFGF) or fibroblast growth factor 2 (FGF2), and wherein the growth medium is without animal serum and without exogenous or added bone morphogenic proteins BMP2, BMP4 and BMP7, thereby producing a cell population in which a proportion of the cells are committed to ectoderm differentiation; and culturing or growing the cell population or a portion thereof produced thereby in non-adherent conditions (e.g., suspension) in a growth medium for an additional period of about 5 to 10 days, wherein the growth medium comprises basic fibroblast growth factor (bFGF) or fibroblast growth factor 2 (FGF2), wherein the growth medium is without animal serum and without bone morphogenic proteins BMP1 and BMP4, and wherein the medium is changed one or more times every 12 to 72 hours or provided by a continuous flow system, thereby producing a cell population in which a proportion of the cells are neuronal progenitor cells. In further various aspects, an adherent substrate includes laminin, fibronectin, Matrigel.TM., gelatin, collagen, collagen IV, poly-lysine, Poly-D-Lysine, poly-ornithine, heparan sulfate proteoglycans, entactin or a combination thereof.

Medium appropriate for culture or growth of the cells include liquid medium (e.g., DMEM, MEM, F12 or a mixture thereof). The medium can include or exclude, as appropriate, among other things: essential amino acids, non-essential amino acids, a vitamin (e.g., a B vitamin, such as B6, B12), a sugar or carbon source, an anti-oxidant, a trace mineral (e.g., selenium, selenite or magnesium), a fatty acid; a hormone; a growth factor (e.g., such as FGF2 between about 4-10 ng/ml, BMP1, BMP4, Noggin between about 5-20 ng/ml, retinoic acid or a retinoic acid receptor agonist between about 5-20 μm); a cytokine, insulin or transferrin. Medium can changed as needed, for example, the growth or culture medium during the period of about 1-7 days can be changed one or more times every 12 to 72 hours or be provided by a continuous flow system In an additional embodiment, after the period of about 1-7 days, neuronal progenitor cells are dissociated from the substrate (e.g., with an enzyme). Neuronal progenitor cells are characterized, for example, as forming a multi-cellular layer in an adherent substrate, or forming cell aggregates in a non adherent condition, of about 25-500 neuronal progenitor cells. After dissociation, the cells or a portion thereof therefrom are optionally cultured or grown in a non-adherent condition or suspension, or an adherent condition. In a particulars aspect, after dissociation non-aggregating cells, fibroblasts or non-viable cells can be removed, reduced in numbers or separated from (e.g., by sedimentation) the cell aggregates.

In a further embodiment, after the period of about 1-7 days, or following dissociation of the cell aggregates or the portion thereof, or following culturing or growing the dissociated cell aggregates or the portion thereof, cells committed to ectoderm differentiation or neuronal progenitor cells are isolated or purified. Such cells can again be identified as forming cell aggregates in suspension (non-adherent conditions) or a multi-cellular layer in an adherent substrate.

In a still further embodiment, such isolated or purified neuronal progenitor cells can then be expanded, propagated or proliferated in a culture or growth medium comprising an adherent condition or non adherent condition (e.g., or suspension), thereby increasing numbers of neuronal progenitor cells. Nueronal progenitor cells can once again be identified as forming cell aggregates in suspension (non-adherent conditions) or a multi-cellular layer in an adherent substrate, and can then optionally be purified or isolated and subjected to additional propagation/proliferation/expansion, differentiation, plating or disposing on a plate, dish, flask, or bottle, or manipulation (e.g., genetic).

In various embodiments of the invention, neuronal progenitor cells in the culture, at least about 50%, 60%, 70%, 75%, 80%, 85%, 90%, 95% or more of the total number of cells in a culture, population or composition are neuronal progenitors (e.g., characterized by transient or stable expression of a neuronal progenitor cell marker or the ability to differentiate into mature neurons). In additional various embodiments of the invention methods, less than about 50%, 40%, 30%, 25%, 20%, 15%, 10% or 5% of the cells do not express a neuronal marker in the cell culture, population or composition. Exemplary developmental markers include, but are not limited to: HNF3β, Pax3, Pax6, Shh, Lhx3, Chx10, Pax7, H4C4 (CD44), VIN-IS-53, AC4, FP3, NOT1, Wnt1, ChAT, Isl1, nestin, MAP2, NF200, Tuj1 and NeuN.

In further various embodiments of the invention, numbers of non-neuronal progenitor cells in the culture, population or composition, such as astrocytes, oligodendrocytes, fibroblasts can be less than the number of neuronal progenitor cells. In particular aspects, there are less than about 30%, 25%, 20%, 15%, 10% or 5% astrocytes, oligodendrocytes, or fibroblasts in the non-neuronal progenitor cells, cell culture, cell population or cell composition Neuronal progenitor cells of the invention include cells transformed or transfected with a nucleic acid sequence that is not typically expressed in a non-transformed or non-transfected neuronal progenitor cell. Such transformed or transfected cells include cell cultures, populations and compositions thereof and progeny cells. Such nucleic acids can encode proteins, polypeptides and peptides, for example, proteins, polypeptides and peptides to substitute for defectiveness, absence or deficiency of endogenous protein, polypeptide or peptide in a subject.

A "nucleic acid" or "polynucleotide" refer to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. Exemplary nucleic acids include RNA, DNA, cDNA, genomic nucleic acid, naturally occurring and non naturally occurring nucleic acid, e.g., synthetic nucleic acid.

Nucleic acids can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. Shorter polynucleotides are commonly referred to as "oligonucleotides" or "probes" of single- or double-stranded DNA.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as yeast or bacteria, a eukaryote such as an animal or mammalian cell or in a plant).

Nucleic acids can be included within vectors as cell transfection typically employs a vector. The term "vector," refers to, e.g., a plasmid, virus, such as a viral vector, or other vehicle known in the art that can be manipulated by insertion or incorporation of a polynucleotide, for genetic manipulation (i.e., "cloning vectors"), or can be used to transcribe or translate the inserted polynucleotide (i.e., "expression vectors"). Such vectors are useful for introducing polynucleotides in operable linkage with a nucleic acid, and expressing the transcribed encoded protein in cells in vitro, ex vivo or in vivo.

A vector generally contains at least an origin of replication for propagation in a cell. Control elements, including expression control elements, present within a vector, are included to facilitate transcription and translation. The term "control element" is intended to include, at a minimum, one or more components whose presence can influence expression, and can include components other than or in addition to promoters or enhancers, for example, leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, among others.

Vectors can include a selection marker. A "selection marker" or equivalent means a gene that allows the selection of cells containing the gene.

"Positive selection" refers to a process whereby only cells that contain the positive selection marker will survive upon exposure to the positive selection agent or be marked. For example, drug resistance is a common positive selection marker; cells containing the positive selection marker will survive in culture medium containing the selection drug, and those which do not contain the resistance gene will die. Suitable drug resistance genes are neo, which confers resistance to G418, or hygr, which confers resistance to hygromycin, and puro which confers resistance to puromycin, among others. Other positive selection marker genes include genes that allow the identification or screening of cells. These genes can encode fluorescent proteins, lacZ, the alkaline phosphatase, and surface markers such CD8, among others.

"Negative selection" refers to a process whereby cells containing a negative selection marker are killed upon exposure to an appropriate negative selection agent which kills cells containing the negative selection marker. For example, cells which contain the herpes simplex virus-thymidine kinase (HSV-tk) gene are sensitive to the drug gancyclovir (GANC). Similarly, the gpt gene renders cells sensitive to 6-thioxanthine.

Vectors included are those based on viral vectors, such as retroviral (lentivirus for infecting dividing as well as non-dividing cells), foamy viruses (U.S. Pat. Nos. 5,624,820, 5,693,508, 5,665,577, 6,013,516 and 5,674,703; WO92/05266 and WO92/14829), adenovirus (U.S. Pat. Nos. 5,700, 470, 5,731,172 and 5,928,944), adeno-associated virus (AAV) (U.S. Pat. No. 5,604,090), herpes simplex virus vectors (U.S. Pat. No. 5,501,979), cytomegalovirus (CMV) based vectors (U.S. Pat. No. 5,561,063), reovirus, rotavirus genomes, simian virus 40 (SV40) or papilloma virus (Cone et al., Proc. Natl. Acad. Sci. USA 81:6349 (1984); *Eukaryotic Viral Vectors*, Cold Spring Harbor Laboratory, Gluzman ed., 1982; Sarver et al., Mol. Cell. Biol. 1:486 (1981); U.S. Pat. No. 5,719,054). Adenovirus efficiently infects slowly replicating and/or terminally differentiated cells and can be used to target slowly replicating and/or terminally differentiated cells. Simian virus 40 (SV40) and bovine papilloma virus (BPV) have the ability to replicate as extra-chromosomal elements (Eukaryotic Viral Vectors, Cold Spring Harbor Laboratory, Gluzman ed., 1982; Sarver et al., *Mol. Cell. Biol.* 1:486 (1981)). Additional viral vectors useful for expression include reovirus, parvovirus, Norwalk virus, coronaviruses, paramyxo- and rhabdoviruses, togavirus (e.g., sindbis virus and semliki forest virus) and vesicular stomatitis virus (VSV) for introducing and directing expression of a polynucleotide or transgene in neuronal progenitor cells or progeny thereof (e.g., daughter cells or mature or differentiated cells).

Nucleic acid can be expressed (transcribed and as appropriate translated) when the nucleic acid is operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates nucleic acid transcription and as appropriate, translation of the transcript.

Promoters and enhancers are particular non-limiting examples of expression control elements. A "promoter sequence" is a DNA regulatory region capable of initiating transcription of a downstream (3' direction) sequence. The promoter sequence includes nucleotides that facilitate transcription initiation. Enhancers also regulate gene expression, but can function at a distance from the transcription start site of the gene to which it is operably linked. Enhancers function at either 5' or 3' ends of the gene, as well as within the gene (e.g., in introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of interest, and stop codons.

Expression control elements include "constitutive" elements in which transcription of an operably linked nucleic acid occurs without the presence of a signal or stimuli. For expression in mammalian cells, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; mouse mammary tumor virus LTR) are used.

Expression control elements that confer expression in response to a signal or stimuli, which either increase or decrease expression of operably linked nucleic acid, are "regulatable." A regulatable element that increases expression of operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased).

Expression control elements include elements active in a particular tissue or cell type, referred to as "tissue-specific expression control elements." Tissue-specific expression control elements are typically more active in specific cell or tissue types because they are recognized by transcriptional activator proteins, or other transcription regulators active in the specific cell or tissue type, as compared to other cell or tissue types.

Neuronal progenitor cells of the invention include cells, cell cultures, cell populations and cell compositions, in which the cells retain viability following delivery, administration, or transplantation/implantation in vivo. In particular embodiments, viability of the total number of progenitor cells or progeny thereof delivered, administered or transplanted, is greater than about 50%, 60%, 70%, 80%, 90%, 95% or 98%, up to 100% after cells are delivered, administered or transplanted in vivo. Viability can vary in duration: 1, 3, 5, 7, 9, 12, 14, 16, 18, 21, 28, 35, 42, 59, 56 or more hours, days, weeks or months following delivery, administration or transplantation/implantation in vivo.

Methods for ascertaining viability in vivo include, for example, identification or detection of expression of a markers in the transplanted region or area. Particular non-limiting examples of markers included, for example, a developmental marker HNF-3b (hepatocyte nuclear factor-3β), Pax3, Pax6, Shh (Sonic Hedgehog), Lhx3 (LIM homeobox protein 3), Chx10 (ceh-10 homeodomain containing homolog), Pax7, H4C4 (hyaluronate receptor, CD44), VIN-IS-53, AC4, FP3, NOT1, Wnt1 (wingless-type MMTV integration site family, member 1), ChAT (choline acetyltransferase), Isl1 (Islet1), nestin, and a neuron marker MAP2 (microtubule associate protein), NF200 (neuro-filament 200), Tuj1 (neuron specific β III tubulin) and NeuN (Neuronal nuclei).

Methods for ascertaining viability in vivo also include, for example, detecting or ascertaining anti-human nuclear labeling, chromosome Y identification, species specific mitochondria identification, DNA fingerprinting of transplanted cells, or expression of a nucleic acid or peptide that identifies the delivered, administered or transplanted/implanted neuronal progenitor cell (e.g., human). Additional methods for ascertaining viability in vivo would be known to the skilled artisan.

Thus, in accordance with the invention, neuronal progenitor cells, including progeny thereof, such as daughter progenitor cells and cells that are more differentiated than the progenitor cells, such as a developmental intermediate cell between a progenitor and a mature neuron, cell populations, cell cultures and cell compositions, can be delivered, administered or transplanted/implanted into a subject. In particular embodiments, neuronal progenitor cells derived from embryonic stem cells (e.g., hESC) are delivered, administered or transplanted/implanted into a living organism (e.g., to the central nervous system) of a subject. In another embodiment, a method for treating a subject in need of increased numbers or function of neuronal progenitor cells, or progeny thereof includes administering, delivering, implanting or transplanting into the subject neuronal progenitor cells, or progeny thereof. In a further embodiment, a method for treating a subject in need of increased numbers or function of neuronal progenitor cells or progeny thereof includes transplanting such cells into a brain or spinal tissue of a subject. In particular aspects, viability of the delivered, administered or transplanted/implanted cells, or progeny thereof is greater than about 50%, 60%, 70%, 80%, 90%, 95% or 98%, up to 100% after cells are delivered, administered or transplanted/implanted.

In accordance with the invention, neuronal progenitor cells, neuronal progenitor cell compositions, or cultures or populations thereof, are used in a therapeutic application wherein the cells can be expected to exhibit one or more functions similar or identical to neuronal progenitor cells, or cells that are derived therefrom. Cells can be administered, delivered, implanted or transplanted using procedures to target the cells to one or more selected regions or sites. In an exemplary embodiment, when cells are administered, delivered or transplanted into spinal cord or brain, the cells may be targeted to spinal cord grey matter, including the dorsal or ventral horn of the grey matter, or any portion of the brain, such a cerebrum, cerebellum, medulla, etc. In another exemplary embodiment, cells can be administered, delivered or transplanted to other regions or sites including, but not limited to, an emerging ventral or dorsal root, a dorsal root ganglion, a spinal nerve, a peripheral nerve a motor nerve, or any other appropriate region or site.

In a non-limiting exemplary method of preparing neuronal progenitor cells and administration, delivery or transplantation/implantation into a subject, neuronal progenitor cells, culture population or composition with a purity greater than 75%, or greater than 80% is typically achieved, which can be further processed or used when confluence reaches 80%, 90%, 100% or even more by multiple layers of cells. In brief, the culture can then be exposed to a proteolytic enzyme (e.g., Trypsin or a similar substitute), which will cause dissociation of the cells and lifting of cells from the adherent substrate. The cell suspension is collected (e.g., in a tube) and the enzyme is contacted with an inhibitor or diluted. The cell suspension can be gently centrifugated and supernatant removed (which steps can be optionally repeated), and cell pellet resuspended in a nutritive media. Cells can be transferred to a non adherent system (e.g., suspension) at a density of about 0.5 to $1 \times 10^6$ cells/ml for 12 to 36 hours (e.g., overnight). A cell count is optionally performed to determine the total number of cells. After transferring the cell culture to the $CO_2$ incubator at about 37° C., cells are typically not disturbed until about 24 hours—if disturbed, the resulting cellular agglomerates can become too large. After this incubation period, cells are typically agglomerated in small clusters of 10 to 100 or 200, or more (e.g., 500) cells. The cell suspension is collected and subjected to centrifugation (e.g., at 80 to 100 rcf for 1-3 minutes). A cell count is performed of the supernatant to determine the number of non-clustered cells. The supernatant is discarded after the count, and the cell clusters are gently resuspended in a crystalloid solution (e.g. HBSS) followed by another centrifugation and cell count of the supernatant.

The total number of clustered cells will be the total number of cells counted a day before (when the nonadherent system was initiated) minus the cells discarded in the supernatant after centrifugation. The final cell pellet is resuspended in a vehicle solution (e.g. HBS) appropriate for in vivo administration, delivery or transplantation/implantation to a desired density. The maximum cell density typically obtained is about 200,000 cells/μl, which is the volume occupied by the cells alone or with minimal vehicle addition. Because of a natural tendency of cell aggregates to sediment, it is recommended to load single doses per administration, delivery or transplantation/implantation site and hold the administration, delivery or transplantation/implantation device horizontal until the administration, delivery or transplantation/implantation is complete.

The terms "subject" and "patient" are used interchangeably herein and refer to animals, typically mammals, such as humans, non-human primates (gorilla, chimpanzee, orangutan, macaque, gibbon), domestic animals (dog and cat), farm and ranch animals (horse, cow, goat, sheep, pig), laboratory and experimental animals (mouse, rat, rabbit, guinea pig). Subjects include disease model animals (e.g., such as mice, rats and non-human primates) for studying in vivo efficacy (e.g., a cardiac disease or disorder animal model). Human subjects include children, for example, newborns, infants, toddlers and teens, between the ages of 1 and 5, 5 and 10 and 10 and 18 years, adults between the ages of 18 and 60 years, and the elderly, for example, between the ages of 60 and 65, 65 and 70 and 70 and 100 years.

Subjects include mammals (e.g., humans) in need of treatment for a neuronal disease or disorder. Subjects also include those at risk of having a neuronal disease or disorder. Target subjects for treatment therefore include those having or at risk of having a neuronal disease or disorder.

The doses or "amount effective" or "amount sufficient" in a method of treatment in which it is desired to achieve a therapeutic benefit or improvement includes, for example, any objective or subjective alleviation or amelioration of one, several or all pathologies, adverse symptoms or complications associated with or caused by the neuronal disease or disorder to a measurable or detectable extent. Thus, in the case of a neuronal disease or disorder, the amount will be sufficient to provide a therapeutic benefit to a given subject or to alleviate or ameliorate a pathology, adverse symptom or complication of the neuronal disease or disorder in a given subject. The dose may be proportionally increased or reduced as indicated by the status of treatment or any side effect(s).

In methods of treatment, a method may be practiced one or more times (e.g., 1-10, 1-5 or 1-3 times) per day, week, month, or year. The skilled artisan will know when it is appropriate to delay or discontinue administration. An exemplary non-limiting dosage schedule is 1-7 times per week, for 1, 23, 4, 5, 6, 7, 8, 9, 10, 15, 20 or more weeks, and any numerical value or range or value within such ranges.

Of course, as is typical for any treatment or therapy, different subjects will exhibit different responses to treatment and some may not respond or respond inadequately to a particular treatment protocol, regimen or process. Amounts effective or sufficient will therefore depend at least in part upon the disorder treated (e.g. the type or severity of the neuronal disease or disorder), the therapeutic effect desired, as well as the individual subject (e.g., the bioavailability within the subject, gender, age, etc.) and the subject's response to the treatment based upon genetic and epigenetic variability (e.g., pharmacogenomics).

Neuronal progenitor cells, cultures, populations and compositions, including progency thereof, can be included in a container, or attached to a substrate. In a particular embodiment, a cell culture includes a substrate to which the cells are attached. Exemplary containers and substrates include tissue culture dishes or plates, flasks, bottles, glass or plastic slides, multiwell plates or dishes having disposed therein neuronal progenitor cells in one or more of the wells.

The invention further provides packaged products and kits, including neuronal progenitor cells or progeny thereof, cell cultures, cell populations and compositions, including, as well as cells, cultures, populations, and compositions enriched or selected for any developmental, maturation or differentiation stage, packaged into suitable packaging material. In various non-limiting embodiments, a packaged product or kit includes neuronal progenitor cells, cultures, populations or compositions, or progeny of neuronal progenitor cells, cultures, populations or compositions, or a mixed population thereof. In various aspects, a packaged product or kit includes a label, such as a list of the contents of the package, or instructions for using the kit e.g., instructions for culturing, expanding (increasing cell numbers), proliferating, differentiating, maintaining, or delivery, administering, implanting or transplanting in vivo, or screening for a compound or agent that modulates a function or activity of neuronal progenitor cells or progeny thereof. In various aspects, a packaged product or kit includes a container, such as a sealed pouch or shipping container, or an article of manufacture, for culturing, expanding (increasing cell numbers), proliferating, differentiating, maintaining, or preserving neuronal progenitor cells or progeny thereof, such as a tissue culture dish, tube, flask, roller bottle or plate (e.g., a single multi-well plate or dish such as an 8, 16, 32, 64, 96, 384 and 1536 multi-well plate or dish). In additional various aspects, a packaged product or kit includes an article of manufacture, for example, an article of manufacture for delivering, administering or transplanting or implanting neuronal progenitor cells or progeny thereof into a subject locally, regionally or systemically.

The term "packaging material" refers to a physical structure housing the product or components of the kit. The packaging material can maintain the components sterilely, and can be made of material commonly used for such purposes (e.g., paper, corrugated fiber, glass, plastic, foil, ampules, etc.). A label or packaging insert can be included, listing contents or appropriate written instructions, for example, practicing a method of the invention.

A packaged product or kit can therefore include instructions for practicing any of the methods of the invention described herein. For example, neuronal progenitor cells or progeny thereof can be included in a tissue culture dish, tube, flask, roller bottle or plate (e.g., a single multi-well plate or dish such as an 8, 16, 32, 64, 96, 384 and 1536 multi-well plate or dish) together with instructions for culturing, expanding (increasing cell numbers), proliferating, differentiating, maintaining, preserving or screening. In an additional non-limiting example, neuronal progenitor cells or progeny thereof can be included in a container, pack, or dispenser together with instructions for delivery, administration, implantation or transplantation into a subject in need thereof.

Instructions may be on "printed matter," e.g., on paper or cardboard within the kit, on a label affixed to the package, kit or packaging material, or attached to a tissue culture dish, tube, flask, roller bottle, plate (e.g., a single multi-well plate or dish such as an 8, 16, 32, 64, 96, 384 and 1536 multi-well plate or dish) or vial containing a component (e.g., neuronal progenitor cells or progeny thereof) of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include cell growth medium, buffering agent, a preservative, or a cell stabilizing agent. Each component of the kit can be enclosed within an individual container or in a mixture and all of the various containers can be within single or multiple packages.

Neuronal progenitor cells and progeny thereof as well as populations, cultures and compositions of neuronal progenitor cells or progeny thereof can be included in or employ pharmaceutical formulations. Pharmaceutical formulations include "pharmaceutically acceptable" and "physiologically acceptable" carriers, diluents or excipients. The terms "pharmaceutically acceptable" and "physiologically acceptable" mean that the formulation is compatible with pharmaceutical administration. Such pharmaceutical formulations are useful for treatment of, or administration or delivery to, or transplanting or implanting into, a subject in vivo or ex vivo.

Pharmaceutical formulations can be made to be compatible with a particular local, regional or systemic administration or delivery route. Thus, pharmaceutical formulations include carriers, diluents, or excipients suitable for administration by particular routes. Specific non-limiting examples of routes of administration for compositions of the invention are parenteral, e.g., intravenous, intraarterial, intradermal, intramuscular, subcutaneous, intra-pleural, injection, transdermal (topical), transmucosal, intra-cranial, intra-spinal, intra-ocular, rectal, oral (alimentary), mucosal administration, and any other formulation suitable for a method or administration protocol.

Neuronal progenitor cells, cultures, populations and compositions, including progeny thereof, can be used to screen for or identify compounds or agents (e.g., drugs) that affect a function or activity of neuronal progenitor cells or progeny thereof. The invention therefore further provides systems for evaluation or identification of a compound or agent that can affect a function or activity neuronal progenitor cells or progeny thereof. Such compounds and agents can be candidates or screened for treatment of a neuronal disease, for example. In one embodiment, a system includes neuronal progenitor and a compound or agent (e.g., drug), wherein the cells and compound or agent (e.g., drug) are in contact with each other.

The invention further provides methods of screening and identifying agents and compounds for modulating an activity or function of neuronal progenitor cells or progeny cells. In one embodiment, a method includes contacting neuronal progenitor cells or progeny thereof with a test agent or compound; and determining if the test agent or compound modulates an activity or function of A test agent or compound modulating an activity or function of neuronal progenitor cells or progeny thereof within the population identifies the test agent or compound as a neuronally active agent. Exemplary activity or function that can be modulated include changes in cell morphology, expression of a marker, differentiation or de-differentiation, maturation, proliferation, viability, apoptosis or cell death neuronal progenitor cells or progeny thereof The term "contacting," when used in reference to cells or a cell culture or method step or treatment, means a direct or indirect interaction between the composition (e.g., cell or cell culture) and the other referenced entity. A particular example of a direct interaction is physical interaction. A particular example of an indirect interaction is where a composition acts upon an intermediary molecule which in turn acts upon the referenced entity (e.g., cell or cell culture).

The term "modulates" an activity or function of neuronal progenitor cells or progeny cells refers to detecting effects on cell activity or function that has been determined to be relevant to a particular use of the neuronal progenitor cells or progeny cells of the invention. Exemplary activities and functions include, but are not limited to, measuring morphology, developmental markers, differentiation, proliferation, viability, cell respiration, mitchondrial activity, membrane integrity, or expression of markers associated with certain conditions. Accordingly, a compound or agent (e.g., a drug candidate) can be evaluated for its effect on neuronal progenitor cells or progeny cells, by contacting neuronal progenitor cells or progeny cells with the compound or agent and measuring any modulation of an activity or function of neuronal progenitor cells or progeny cells as disclosed herein or would be known to the skilled artisan.

Methods of screening and identifying agents and compounds include those suitable for high throughput screening, which include arrays of cells (e.g., microarrays) positioned or placed, optionally at pre-determined locations or addresses. High-throughput robotic or manual handling methods can probe chemical interactions and determine levels of expression of many genes in a short period of time. Techniques have been developed that utilize molecular signals (e.g., fluorophores) and automated analyses that process information at a very rapid rate (see, e.g., Pinhasov et al., Comb. Chem. High Throughput Screen. 7:133 (2004)). For example, microarray technology has been extensively utilized to probe the interactions of thousands of genes at once, while providing information for specific genes (see, e.g., Mocellin and Rossi, Adv. Exp. Med. Biol. 593:19 (2007)).

Such screening methods (e.g., high-throughput) can identify neuronally active agents and compounds. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, siRNA libraries, and adenoviral transfection vectors.

Screening methods are also applicable to predictive toxicology. The use of neuronal progenitor cells or progeny thereof positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for high-throughput or high content screening using small molecule libraries, siRNA libraries, adenoviral transfection vectors, and gene based microarray approaches can identify various therapeutic and cardiac liability targets. Such techniques also allow direct high-throughput measurement of cardiac intervention strategies by means of fluorescent reporter dyes and biomarkers for cell health and morphological phenotype, expression of fluorescent reporter proteins, various FRET approaches and direct measurement of electrophysiological currents in live cells. neuronal progenitor cells or progeny thereof.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, Genbank accession numbers and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to a "neuronal progenitor cell" includes a plurality of cells, or a population of cells, and reference to "a population of neuronal progenitor cells having a purity of greater than about 70% neuronal progenitor cells" can include multiple cell types of varied developmental, maturation or differentiation stage within the population; likewise, reference to cell populations or cell cultures or cell compositions, and during methods of producing neuronal progenitor cells, such cells can include multiple cell types of varied developmental, maturation or differentiation stage within the population.

A "subject" can be any animal, in a particular example, a human. A "patient" can be any animal, in a particular example, a human.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes any numerical value or range within or encompassing such values, such as 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and any numerical range within such a range, such as 90-92%, 90-95%, 95-98%, 96-98%, 99-100%, etc. In an additional example, reference to greater or less than a particular percent, e.g., greater than 25% means 26%, 27%, 28%, 29%, 30%, 31%, . etc. up to 100%; and less than 25% means 24%, 23%, 22%, 19%, 18%, 17%, . . . etc., to 0%.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. For example, it may be desired to exclude one or more components from the various cell culture and growth mediums disclosed herein. It may also be desired to exclude or omit one or more method steps, such as cell expansion/propagation or purification from the various methods disclosed herein. Thus, even though the invention is generally not expressed herein in terms of what the invention excludes or omits, such embodiments of the invention are included.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example includes a description of embryonic stem cell differentiation and characterization.

Human embryonic stem cells were expanded using media and substrates previously described in 150 cm square culture flasks. The initiation of differentiation was performed by replacing the stem cell media with the chemically defined media with the following content: DMEM:F12-480 ml; B27 supplement—10 ml; Insulin—Transferrin—Selenite supplement—5 ml; Magnesium chloride 0.5M -0.5 ml; Glutamax 5 ml; and FGF 5 ng/ml added at cell feeding.

In the second day of differentiation, retinoic acid dissolved in dimethylsulfoxyde was added at a concentration of 10 µM. The media was replaced daily.

At day 7 of differentiation the culture was dissociated with tripsyn-EDTA 0.25% for 3 minutes followed by treatment with trypsin inhibitor and two washes by centrifugation and resuspension in nutritive media. The final cellular suspension was transferred in ultra-low binding 6-well plates (Corning) and placed in the CO2 incubator. After dissociation, the cultures were fed next day and every other day for the duration of the protocol.

At day 21 the cells were transferred on adherent substrate of Matrigel 1:30. Cells were allowed to migrate out of the cellular clumps for the next 7 days and than the cultures were dissociated again using the same enzymatic method described above. The cultures were passaged for another 4 weeks with a splitting ratio of 1:6. The cells were characterized in imaging chambers using immunocytochemistry methods (FIGS. 1A-1H).

Media suitable for neuronal cell cultures and populations, which can be referred to as "neuronal media" or "neuronal media" include formulations I and II, which produced similar results, and are as follows:

Media Formulation 1:
  DMEM:F12-480 ml
  B27 supplement—10 ml
  Insulin—Transferrin—Selenite supplement—5 ml
  Magnesium chloride 0.5M -0.5 ml
  Glutamax 5 ml
  FGF 5 ng/ml added at feeding
  Retinoic acid is added at a concentration of 10 mM daily, in the first 7 days.

Media Formulation 2, for Example 3:
  DMEM:F12 with HEPES—480 ml;
  B27 supplement—10 ml;
  Insulin 10 ug/ml;
  Sodium selenite 5 ng/ml;
  Magnesium chloride 0.5M -0.5 ml;
  Transferrin 25 µg/ml;
  Glutamax 5 ml;
  FGF 5 ng/ml added at feeding
  Retinoic acid is added at a concentration of 10 mM daily, in the first 5 days.

Example 2

This Example includes a description of high-throughput screening plates using neuronal progenitor cells.

In this example cells were seeded into 96-well and 384-well plates and retained viability when shipped worldwide. Cells in this format remained viable for up to 1 week after shipping at the end user, which allowed various studies (e.g., drug screening) and automated imaging. This system is a ready to use, assay-ready screening plate seeded with high-purity human cells derived from any stem cell type.

Human embryonic stem cell (hESC) cultures were allowed to differentiate into neuronal progenitors (NPs) as described above. Briefly, hESCs are expanded on Matrigel (BD Biosciences, San Jose, Calif.) for 1-3 weeks in EctoBias™ media (California Stem Cell, Inc.) supplemented with basic fibroblast growth factor (bFGF), which causes an ectodermal-biased differentiation. Cells are then removed from the adherent substrate, transferred to ultra-low binding 75 $cm^2$ or 225 $cm^2$ or 630 $cm^2$ dishes and suspended in a neuronal differentiation media with the following composition: DMEM:F12 with HEPES—480 ml; B27 supplement—10 ml; Insulin 10 ug/ml; Sodium selenite 5 ng/ml; Magnesium chloride 0.5M -0.5 ml; Transferrin 25 µg/ml; Glutamax 5 ml; FGF 5 ng/ml added at feeding.

Cells were exposed to neuronal differentiation media for 5 days, supplemented with retinoic acid (RA). Cultures were fed daily for the duration of RA treatment and every 2 days for 16 subsequent days. During the feeding procedure the cell suspension was removed from the flask, placed in 50 ml centrifuge tube, left for sedimentation for 10 minutes and the supernatant replaced with fresh media. Following this procedure, the nonviable cells or cells without spherogenic properties are removed from the culture and discarded. The spherogenic property of the neuronal cells is based on the presence of homophilic neuronal cell adhesion molecules (NCAMs) on the surface of the cells. At day 21 of the differentiation protocol, the spherical cell clusters were transferred to Matrigel substrate and exposed to the same neuronal differentiation media. Non-adherent cells were discarded during feeding.

Example 3

This Example includes a description of seeding and maturation in microtiter plates, phenotype analysis and the effect of shipment on viability.

At day 22, the cultures were enzymatically dissociated, quantified for total cell number and viability and resuspended for a density of 1,000,000 cells/ml. This cell suspension was further diluted in 100,000 cells/ml increments. Different densities of human neuronal progenitors were then plated into 96-well plates for a total of 200 ul/well containing one of the following substrates: poly-D-lysine, poly-D-lysine-laminin or Matrigel and left in incubator overnight to allow for proper adherence.

For a 96-well format, the optimal density was found in the range of 20,000-40,000 cells per well in 200 μL of neuronal media. Cells were fed next day by withdrawing 100 μL of media and replacing with fresh neuronal media. Cells were left for one to several (3-5) days to fully adhere and reach a stable mature morphological phenotype. Following this initial period, cells were maintained viably for up to two weeks without the addition of growth factors.

The phenotype of human neuronal progenitors (hNPs) in 96 well plates was characterized using specific immunomarkers for early neuronal progenitors, namely Pax6 and nestin. The ability to further differentiate was evaluated in vitro via immunohistochemistry for neurons using Tuj1, and NeuN. The presence of contaminants, such as astrocytes, was determined using glial fibrillary acidic protein (GFAP).

Immunocytochemical characterization was carried out directly in the microtiter plates and the viability analyzed with the Cellomics HitKit, on automated high-content imaging systems. The automated image analysis algorithms were used to quantify cell viability and quantification of immuno-histochemical markers. Viability was between about 95% and 98%, with less than about 5% variability between wells.

The protocol described routinely produces typical cultures in which 96-99% cells express Pax-6 or Nestin and less than 1% of the cells are contaminants, mostly astrocytes, expressing GFAP.

Once cells in 96-well plates were fully adherent (after 3 days), wells were filled with media and sealed using sterile Robolids (Corning, USA) to eliminate gas exchange, maintain pH, and avoid contamination/leakage. Other successful methods of sealing the plates include polypropylene molds and adhesive foil. Plates were vacuum sealed in a sterile polyethylene bag with a pad of absorbent material and finally heat-sealed in a Mylar foil bag to prevent light exposure and thermal stability. The packaging meets the requirements for shipping hazardous biological material.

Individually sealed plates were placed in a 2 inch wall Styrofoam shipping container lined with 22-28° C. phase-change material (TCP Inc.). The temperature logger placed inside of the packaging showed stable temperature reading around 24 C for up to 36 hours. To test various shipping conditions, seasonal studies were done to show stability at various external temperatures by shipping the package from Irvine, Calif. to Boston, Mass. Longer shipping studies included 48 hour airfare to Netherlands in various seasonal conditions. At destination over 95% of the cells were found to maintain the morphology, adherence to the substrate, phenotype and viability.

Example 4

This Example includes a description of transplantation studies into central nervous system of live animals.

To study the ability of neuronal progenitor cells to terminal differentiate in vivo, neuronal progenitors were transplanted into injured or non-injured rat spinal cord. Progenitor cells were enzymatically dissociated at day 28 of differentiation and concentrated to 50,000 cells/μl. Using 10 μl Hamilton syringes and 33G needle, cells were injected in the cervical spinal cord of rats at total volume of 2, 4 and 8 microliters corresponding to 100,000, 200,000 and 400,000 respectively. The animals survived for 60 days, then were euthanized and the spinal cord collected for analysis.

Immunohistochemistry was performed using antihuman nuclear antibody and neuron specific marker (Tuj-1, Map2). In the transplanted animals, neurons matured and extended processes in bundles of human axons and dendrites. The transplanted cells did not form tumors nor exhibit over-proliferation. Animal behavior data indicated no loss or detrimental effects of the transplanted cells on the host. Further studies will confirm the presence of a beneficial effect in animal models with neuronal loss (in the spinal cord or brain).

What is claimed:

1. A method of producing a population of neuronal progenitor cells, comprising:
   a) culturing embryonic stem cells, sourced from totipotent cells, in a growth medium comprising basic fibroblast growth factor (b(FGF) or fibroblast growth factor 2 (FGF2) and retinoic acid for a period of about 1-7 days, wherein the growth medium is without animal serum and without bone morphogenic proteins BMP4 and BMP7;
   b) culturing the cell population of step a) in suspension (non-adherent conditions) in a growth medium for an additional period of about 5-10 days wherein the growth medium comprises basic fibroblast growth factor (bFGF) or fibroblast growth factor 2 (FGF2), to form aggregates comprising isolated neuronal progenitor cells, wherein the growth medium is without animal serum and without bone morphogenic proteins BMP4 and BMP and wherein the medium is changed one or more times every 12 to 72 hours or provided by a continuous flow system, thereby producing a cell population in which at least 75% of the cells are neuronal progenitor cells; and
   c) identifying cells within the population that express pax6 and nestin, and NeuN and Tuj1,
   wherein at least 90% of the population of human neural progenitor cells express Pax6 and nestin and also express at least one of NeuN and Tuj1.

2. The method of claim 1, wherein at least about 90% of the cell population are neuronal progenitor cells.

3. The method of claim 1, wherein at least about 95% of the cell population are committed to neuronal progenitor cells.

4. The method of claim 1, wherein following culturing the cell population of step a) in an adherent substrate for about 1-7 days, the cells are enzymatic dissociated from the substrate prior to culturing the cell population in a non-adherent condition or suspension.

5. The method of claim 1, wherein the aggregates comprise about 25-500 neuronal progenitor cells.

6. The method of claim 1, further comprising step d), removing non-aggregating cells.

7. The method of claim 1, further comprising following steps a) or b), isolating or purifying the cells which are committed to neuronal progenitor cells.

8. The method of claim 1, further comprising step d), isolating or purifying the neuronal progenitor cells.

9. The method of claim 1, further comprising step d), proliferating the neuronal progenitor cells in a growth medium comprising a suspension culture, thereby increasing numbers of neuronal progenitor cells.

10. The method of claim 1, further comprising step d), isolating one or more of said neuronal progenitor cells and transferring the one or more cells into a growth medium comprising suspension culture.

11. The method of claim 1, wherein there are less than about 10% in aggregate of astrocytes, oligodendrocytes, fibroblasts, or glial cells in the culture.

12. The method of claim 1, wherein there are less than about 10% in aggregate of cells that do not express both a developmental marker and a neuron marker in the culture.

13. The method of claim 1, wherein at least 75% of said cell population stably or transiently express at least one of the developmental markers and one neuron marker, the developmental marker selected from the group consiting of: HNF-3β, Pax3, PAx6, Shh, Lhx3, Chx10, Pax7, H4C4, VIN-IS-53, AC4, FP3, NOT1, Wnt1, and IsIand nestin and the neuron marker selected from the group consisting of MAP2 (microtubule associate protein), NF200 (neuro-filament 200), Tuj 1 (neuron specific beta tubulin) and NeuN (Neuronal nuclei).

14. The method of claim 1, wherein at least a proportion of said cells exhibit one or more of the following characteristics: a small oval or triangular cell shape with minimal cytoplasm; unipolar or bipolar with short expansions/processes optionally with a spliced termination; active cell division on the longitudinal axis; a polarized orientation; limited migratory ability; or form a multi-cell layered structure on an adherent substrate or a cell agglomerate in suspension.

* * * * *